United States Patent

Suyama

Patent Number: 5,127,828
Date of Patent: Jul. 7, 1992

[54] ORTHODONTIC APPLIANCE

[76] Inventor: Hajime Suyama, 6-1, Wachigawara 2-chome, Miyazaki-shi, Japan

[21] Appl. No.: 659,245

[22] Filed: Feb. 22, 1991

Related U.S. Application Data

[63] Continuation of Ser. No. 446,202, Dec. 5, 1989, abandoned.

[51] Int. Cl.$^5$ .............................................. A61C 3/00
[52] U.S. Cl. ............................................................. 433/8
[58] Field of Search .................................... 433/8, 9, 16

[56] References Cited

U.S. PATENT DOCUMENTS

| | | | |
|---|---|---|---|
| 3,496,637 | 2/1970 | Etengoff | 32/14 |
| 4,242,085 | 12/1980 | Wallshein | 433/14 |
| 4,299,569 | 11/1981 | Frantz | 433/8 |
| 4,322,206 | 3/1982 | Reynolds | 433/9 |
| 4,917,602 | 4/1990 | Broussard | 433/8 |

Primary Examiner—Gene Mancene
Assistant Examiner—Cindy A. Cherichetti
Attorney, Agent, or Firm—Sheridan Ross & McIntosh

[57] ABSTRACT

In an orthodontic appliance comprising a plurality of brackets for correcting misaligned teeth, each secured to a surface of a tooth and a wire for connecting the plurality of brackets to each other in the direction of a set of teeth, each bracket comprises a substrate to be attached at its one surface to the tooth surface and at least one wire support disposed on the other surface of the substrate and defining a groove recessed therein for passing the wire slidably along the direction of the set of teeth, in which the inner wall surface of the recessed groove is inwardly protruded convexly as a curved surface relative to the direction of passing the wire. An operation period required for correcting misaligned teeth can be shortened remarkably since the teeth can move smoothly owing to the reduced friction between the wire and the groove of the bracket.

11 Claims, 4 Drawing Sheets

ORTHODONTIC APPLIANCE

This is a continuation of application Ser. No. 07/446,202, abandoned, filed Dec. 5, 1989.

BACKGROUND OF THE INVENTION

1. Field of the Invention

The present invention concerns an orthodontic appliance and, more specifically, it relates to an improved structure of a bracket used in such an appliance for correcting misaligned teeth.

2. Description of the Prior Art

A person's teeth greatly influence his or her looks and facial features, in addition to their important role in chewing food. Therefore, recently, the number of people, especially young women, who worry about their misaligned teeth and thus become negative in personal relationship has been increasing. Most patients consulting orthodontists complain about their appearance.

A typical orthodontic appliance comprises a plurality of brackets to be fixed to the surfaces of teeth and a metal wire for connecting those brackets to each other along the direction of a set of teeth.

As the bracket used for the appliance of this type, there has been known a so-called "edgewise bracket" comprising a base plate and a pair of wire supports which are disposed along the two lateral ends of the base plate and which define a square groove recessed laterally into the center of each support.

For correcting misaligned teeth by using the orthodontic appliance described above, for instance, a first premolar just behind a canine is extracted to make room and then the bracket is fixed to the surface of each of the teeth. Then a wire is laterally extended under tension through the groove of each bracket and both ends of the wire are fixed to a pair of first molars. Further a rubber band is stretched between the brackets appended to the canine and the first molar.

Thus, the bracket fixed to the tooth and the wire move slidingly relative to each other to correct the misaligned teeth with lapse of time.

However, correction of the misaligned teeth actually takes a considerable period of time, because the relative movement between the wire support of the bracket and the wire is not smooth.

Incidently, since the appearance of a patient with brackets on his teeth is not very good, it is desirable to shorten the period of tooth correction.

Considering that one of the major factors which extends the correction period is friction between the recessed grooves and the connection wire, the present inventor has studied how to reduce this friction.

SUMMARY OF THE INVENTION

The object of the present invention is to overcome the problems described above and provide an orthodontic appliance capable of contributing to the shortening of the period of tooth correction.

The foregoing object of the present invention can be attained by an orthodontic appliance comprising a plurality of brackets for correcting misaligned teeth, each secured to a surface of a tooth and a wire for connecting the plurality of brackets to each other in the direction of a set of teeth, wherein each of the brackets comprises:

a substrate to be attached at its one surface to the surface of the tooth and at least one wire support which is disposed on the other surface of the substrate and which defines a groove recessed therein for passing the wire slidably along the direction of the set of teeth, in which the inner wall surface of the recessed groove is inwardly protruded convexly as a curved surface relative to the direction of passing the wire.

The curved surface at the inside of the recessed groove may be formed on both of the side walls and/or a bottom wall of the groove.

The curved surface may be in the form of an arc or in the form of an arc whose crest is partially flattened.

Since the bracket and the wire can be brought into point-to-point contact with each other at the protruded curved surface of the groove, the wire can slide smoothly along the grooves in the bracket bonded to each of the teeth and the period required for correcting the misaligned teeth can be reduced remarkably.

BRIEF DESCRIPTION OF THE ACCOMPANYING DRAWINGS

DESCRIPTION OF THE PREFERRED EMBODIMENTS

Preferred embodiments of the present invention will be described in detail in comparison to a conventional appliance while referring to the accompanying drawings.

Figure 1:
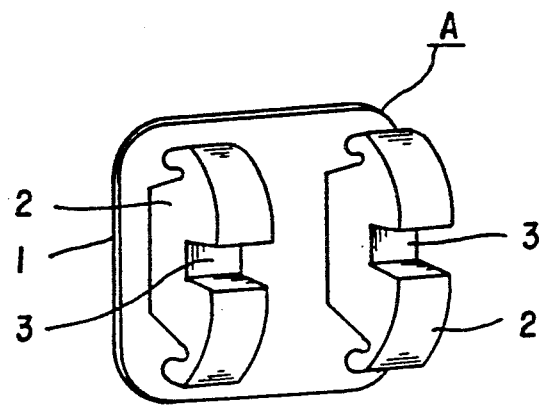
FIG. 1 is a perspective view of a conventional bracket used in an orthodontic appliance for correcting a misaligned tooth.
Figure 2:
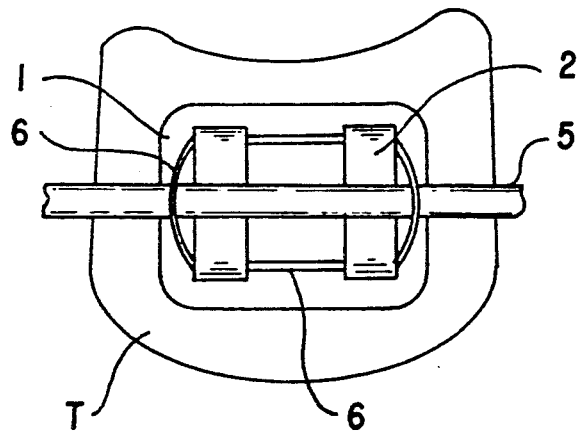
FIG. 2 is a front elevational view showing a state wherein the bracket is bonded and fixed to the surface of a tooth.
Figure 3:
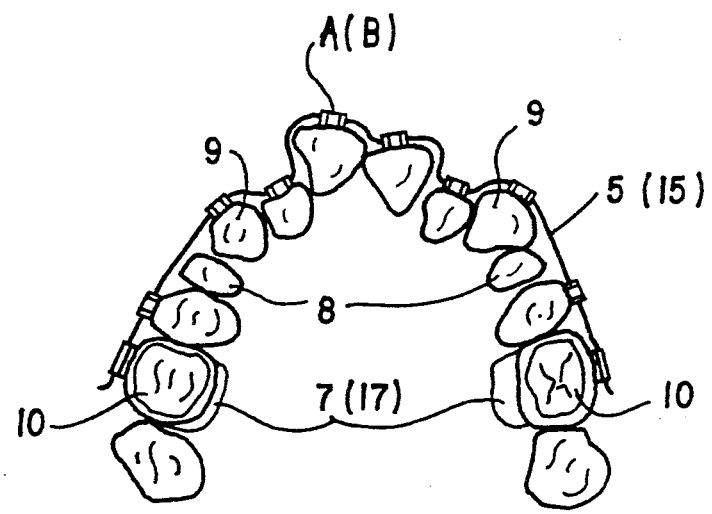
FIG. 3 is an explanatory view showing a state of correction.

First a conventional orthodontic appliance is to be outlined referring to FIG. 1 through FIG. 3.

An edgewise bracket A shown in FIG. 1 comprises a base plate 1 and a pair of wire supports 2 and 2 each of which is disposed along the lateral end of the base plate 1. A square groove 3 is recessed laterally into the center of each wire support 2.

An example of operation for correcting a misaligned tooth using the bracket A will now be described briefly.

Teeth become irregular when the jaw is too small for all of the teeth to erupt neatly, so they push and shove against each other. In order to correct such misaligned teeth, a first premolar 8 just behind a canine 9 is extracted to make room for the other teeth to be forced into place (refer to FIG. 3).

After the first premolar 8 is extracted, a plurality of the brackets A, A —— are bonded and fixed to the surfaces of predetermined teeth. Subsequently, a round wire 5 made of stainless steel is laterally extended under tension through the groove 3 of each of the brackets A and both ends of the wire 5 are fixed to bands 7 which are wound around a pair of first molars 10 respectively (on the right and left sides). The round wire 5 is urged by a fixing wire 6 to the bracket A so that the wire 5 cannot come out of the grooves 3 (refer to FIG. 2).

Once the brackets A and the round wire 5 are thus attached, each of the teeth is moved by the elastic force of the round wire 5 with the lapse of time so that irregularities along the direction of tooth thickness (hereinafter referred to as the thickness direction) are corrected.

Although the space formed by the extraction of the tooth is somewhat reduced by this process, it cannot since be completely closed only by that. Therefore, in order to close the gap in the teeth in the direction along the set of teeth (hereinafter simply referred to as the lateral direction), a rubber band (not illustrated) is stretched between the bracket A which is bonded and fixed to the canine 9 and the band 7 which is wound around the first molar 10 to move the canine 9 toward the first molar 10 by the elastic force of the rubber band. In this case, since the round wire 5 slides along the grooves 3 of the bracket A which is bonded and fixed to the canine 9, the canine 9 is moved toward the first molar 10, or vice versa.

However, correction of the misaligned teeth by the appliance in the prior art requires, a considerable period as described above.

This is attributable to the friction between the round wire 5 and the inner wall of the groove 3 of the bracket 1, which hinders smooth sliding between them.

Then, it is intended in the present invention to reduce the friction between the outer circumference of the wire and the inner wall surface of the groove as much as possible, thereby enabling smooth movement of the teeth.

EXAMPLE

Examples of the present invention will be described below with reference to preferred embodiments shown in FIG. 4 through FIG. 8.

Figure 4:
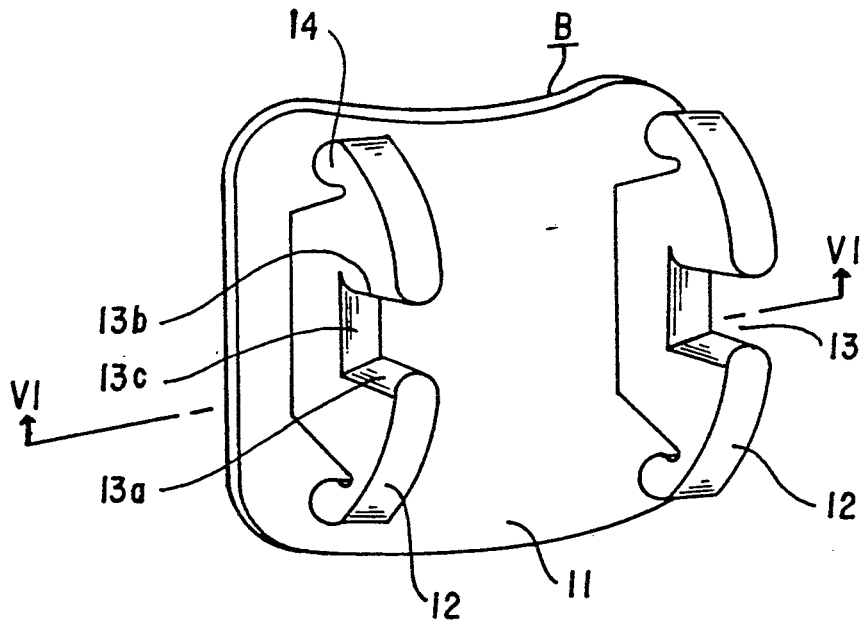
FIG. 4 is a perspective view of a bracket used in an orthodontic appliance according to the present invention.
Figure 5:
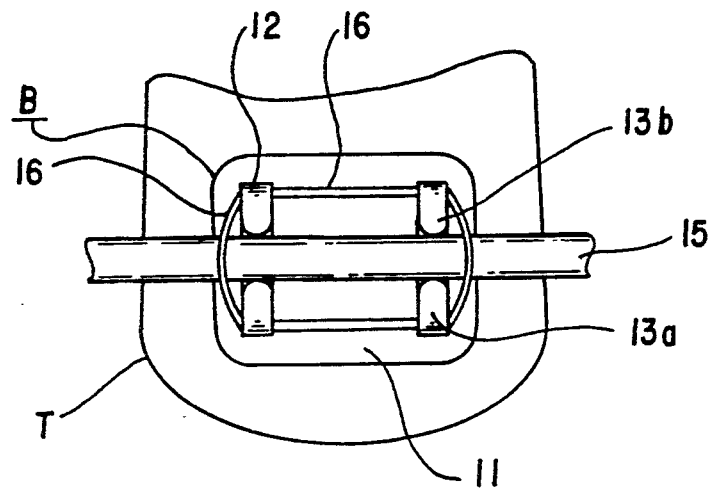
FIG. 5 is a front elevational view showing a state wherein the bracket of FIG. 3 is bonded and fixed to the surface of a tooth.

As shown in FIG. 4, a bracket B comprises a base plate 11 for bonding and fixing to the surface of a tooth and a pair of wire supports 12 and 12 each of which is disposed along the lateral end of the base plate 11.

Figure 6:
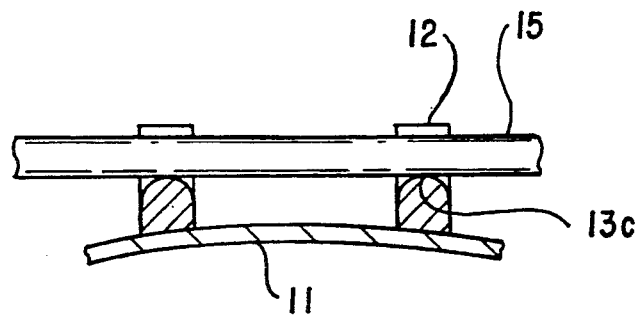
FIG. 6 is a cross sectional view taken along the line VI—VI of FIG. 4.

The entire base plate 11 is curved slightly so that it can fit against the surface of the tooth (refer to FIG. 6). A groove 13 is recessed laterally in the central portion of each wire support 12 (refer to FIG. 4), and a round wire 15 is passed through the groove 13. A stopping hook 14 extends from each end upper of the wire support 12. A fixing wire 16 is firmly set to the bracket B while being passed beneath the stopping hook 14 and over the upper surface of the round wire 15 to fix the latter (refer to FIG. 5).

In this embodiment, each of the inner side walls 13a and 13b of the groove 13 has a semi-circular cross section. More in particular, in the cross section shown in FIG. 5, each of the side walls 13a and 13b is formed into such a convex protruding to the inside of the groove 13 relative to the direction of the wire passage, so that the round wire 15 is brought into point-to-point contact with each of the side walls 13a and 13b of the grooves at the crest thereof 13 when the round wire 16 is laterally passed through the groove 13.

In addition, the bottom surface 13a of each groove 13 also has a semi-circular shape i.e., a semi-cylindrical form extended between the walls 13a and 13b. More in particular, in the cross section shown in FIG. 6, the bottom wall 13c is formed into such a convex protruding to the inside of the groove 13 relative to the direction of the wire passage, so that the round wire 15 is also brought into point-to-point contact with the bottom surface 13c of each groove 13.

Now the operation of the illustrated embodiment will be explained.

As shown in FIG. 3, i.e., in the same way as in the conventional bracket described above, after a first premolar 8 is extracted, the bracket B is bonded and fixed to the surface of each of predetermined teeth by using a resin type adhesive. Subsequently, a round wire 15 is stretched laterally through the grooves 13 of each of the brackets B, and both ends of the wire 15 are fixed to bands 17 which are wound around the first molars 7 respectively (on the right and left sides).

In this case, the round wire 15 is prevented from coming out of the groove 13 by the fixing wire 16 that is firmly wound around the bracket B in such a manner that it presses against the upper surface of the round wire 15 and is passed below the stopping hooks 14.

Finally, a rubber band (not illustrated) is stretched between the bracket B which is bonded and fixed to the canine 9 and the band 17 which is wound around the first molar 10.

When the appliance is thus attached, the teeth are moved by the elastic force of the round wire 15 to straighten irregularities in the thickness direction, and the canine 9 is moved toward the first molar 10 by the elastic force of the rubber band to completely close the gap formed by extracting the tooth. Since the round wire 15 can slide along the grooves 13 of the bracket B which is bonded and fixed to the canine 9, the canine 9 is moved toward the molar 10.

In this case, since the inner surfaces of both of the side walls 13a and 13b and the bottom wall 13c of each groove 13 recessed in the wire supports 12, 14 are circularly curved, the outer circumference of the round wire 15 and the inner circumference of the grooves 13 are brought into point-to-point contact with each other.

Frictional resistance can thus be greatly reduced when compared with the conventional case, in which the wire has been brought into sliding contact over the entire lateral length of the inner wall of the groove. Accordingly, the round wire 15 can slide smoothly along the grooves 13 of the bracket B, which can remarkably shorten the period required for the correction of misaligned teeth.

In the embodiment of the present invention being thus constituted, since the groove in the bracket B and the round wire 15 can be brought into point-to-point contact with each other as described above and, accordingly, the round wire 15 can slide smoothly along the grooves 13 in the brackets B which are bonded and fixed to the respective teeth to be moved, the period required for correcting the misaligned teeth can be greatly reduced, when compared with the conventional case. Further, the present invention also has an effect that the grooves are less likely to become chipped because the surfaces of the grooves are smoothly curved, even when the bracket is made of ceramic or hard resin as is often used at present and which tends to chip easily.

In practical orthodontic operation for the correction of the misaligned teeth, a round wire of a smaller diameter has been used at an initial step of the operation and then the wire is successively replaced with wires of greater diameters for correcting vertical irregularity. Then, a square-sectioned wire is finally used for applying more effective correcting force.

Figure 7:
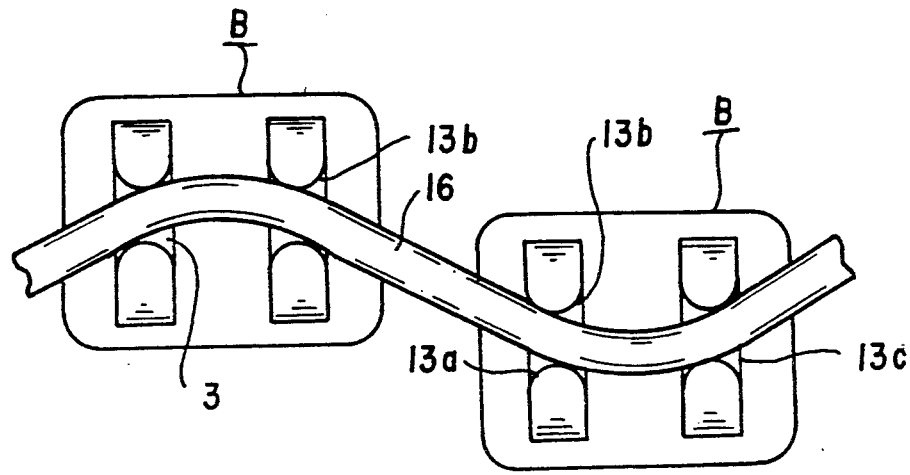
FIG. 7 is a front elevational view where a square-sectioned wire is passed through the groove of the brackets.
Figure 8:
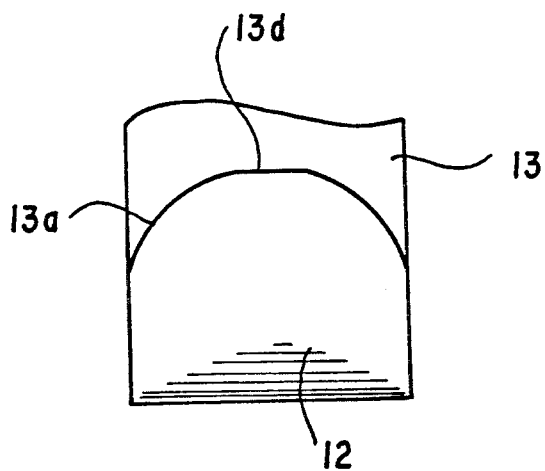
FIG. 8 is an enlarged cross sectional view illustrating the bottom wall of a modified bracket.

In the embodiment of the present invention, since the inner wall surface of each of the grooves recessed in the bracket is smoothly curved, even such a square-sectioned wire can be used already from the initial step of the operation, because the wire can be bent smoothly along the curved surface as shown in FIG. 7. It will be apparent that such a smooth bending of the square-sectioned wire is very difficult along the flat-walled groove of the bracket A as shown in FIG. 1.

It is accordingly possible by the appliance of the present invention to use the square-sectioned wire at any step, for example, even at the initial step of the operation, thereby saving labors of replacing various kinds of wires and, thus, further shortening the correction period.

In the embodiment according to the present invention, the correction period can be shortened, while different depending on the cases, by about 20 to 30% in average as compared with conventional cases.

The semi-circular cross-sectional shape of the inner groove walls 13a–13c may be modified in any other form as long as the friction between them and the wire can be reduced. For example, a semi-circular shape, the top of which is partially flattened may be used as shown at 13d in FIG. 8. Accordingly, "curved surface" in the present invention also include such a substantially curved surface.

What is claimed is:

1. An improved edgewise orthodontic bracket having at lest one pair of spaced apart and oppositely facing tie wings, said at lest one pair of tie wings having opposing wall portions to define at least a portion of a mesiodistal archwire slot which opens labially, the improvement comprising:
    first and second protruding base portions spaced apart in said archwire slot, an outer surface of each of said first and second protruding base portions being substantially curved outwardly, said outer surfaces of said first and second protruding base portions extending between said opposing wall portions and having longitudinal axes transverse to a mesiodistal axis through said archwire slot, wherein frictional contact is reduced between said bracket and an archwire positioned in said archwire slot.

2. The improved bracket of claim 1, wherein said substantially curved outer surfaces of said first and second protruding base portions are convex.

3. The improved bracket of claim 1, wherein a portion of at least one of said opposing wall portions adjacent to one of said outer surfaces has a substantially outwardly curved wall surface facing into said archwire slot.

4. The improved bracket of claim 3, wherein:
    a portion of each of said opposing wall portions adjacent to one of said outer surfaces includes a substantially outwardly curved wall surface facing into said archwire slot.

5. The improved bracket of claim 3, wherein said substantially outwardly curved wall surface is convex.

6. The improved bracket of claim 1, further comprising:
    two pair of spaced apart and oppositely facing said tie wings defining a slot therebetween, wherein each of said two pair of said tie wings includes opposing wall portions to define at least a portion of said archwire slot, wherein wall surfaces of said opposing wall portions adjacent to said outer surfaces of said first and second protruding base portions are substantially curved outwardly into said archwire slot.

7. The improved bracket of claim 1, wherein an archwire positioned in said archwire slot contacts each of said outer surfaces only along at least a portion of a line which is substantially parallel to said longitudinal axis of said outer surface.

8. An edgewise orthodontic bracket, comprising:
    a substrate for attachment to a tooth or band; and
    at least two pair of spaced apart and oppositely facing tie wings affixed to said substrate, said tie wings defining a mesiodistally extending archwire slot opening labially and passing through said tie wings, said slot having in each of said tie wings an occlusal sidewall portion, a gingival sidewall portion and a protruding labial base portion, said labial base portion being substantially curved outwardly and having a longitudinal axis transverse to a mesiodistal axis through said slot, said substantially curved labial base portion being convex, wherein frictional contract is reduced between said protruding labial base portion and an orthodontic archwire in said slot.

9. The orthodontic bracket of claim 8, wherein said occlusal and gingival sidewall portions are substantially curved outwardly.

10. The orthodontic bracket of claim 9, wherein said substantially curved sidewall portions are convex.

11. A double edgewise orthodontic bracket, comprising:
    a substrate; and
    two pair of spaced apart and oppositely facing tie wings defining an orthodontic archwire slot therebetween, said slot extending mesiodistally and opening labially, wherein each of said tie wings comprises a sidewall portion substantially curved outwardly and facing into said slot and a labial base portion therebetween, said base portion being substantially curved outwardly and having a longitudinal axis transverse to a mesiodistal axis through said slot, each of said sidewall portions and said base portions being convex, wherein frictional contact is reduced between the bracket and an archwire positioned in said slot.

* * * * *

UNITED STATES PATENT AND TRADEMARK OFFICE
CERTIFICATE OF CORRECTION

PATENT NO. : 5,127,828
DATED : July 7, 1992
INVENTOR(S) : Suyama

It is certified that error appears in the above-identified patent and that said Letters Patent is hereby corrected as shown below:

Column 5, Claim 1, line 34, please delete "lest" and insert therefor -- least --.

Signed and Sealed this

Twenty-first Day of September, 1993

Attest:

Attesting Officer

BRUCE LEHMAN

Commissioner of Patents and Trademarks